US010946174B2

United States Patent
Abu-Sultaneh et al.

(10) Patent No.: US 10,946,174 B2
(45) Date of Patent: Mar. 16, 2021

(54) TUBE SECURING DEVICE

(71) Applicant: Indiana University Research and Technology Corporation, Indianapolis, IN (US)

(72) Inventors: Samer Abu-Sultaneh, Carmel, IN (US); Terri Bogue, Carmel, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 422 days.

(21) Appl. No.: 15/925,829

(22) Filed: Mar. 20, 2018

(65) Prior Publication Data
US 2018/0280662 A1    Oct. 4, 2018

Related U.S. Application Data

(63) Continuation-in-part of application No. 14/860,030, filed on Sep. 21, 2015, now Pat. No. 10,034,971.

(60) Provisional application No. 62/053,328, filed on Sep. 22, 2014.

(51) Int. Cl.
*A61M 25/02* (2006.01)
*A61M 27/00* (2006.01)

(52) U.S. Cl.
CPC .......... *A61M 25/02* (2013.01); *A61M 27/00* (2013.01); *A61M 2025/024* (2013.01); *A61M 2025/028* (2013.01); *A61M 2025/0266* (2013.01); *A61M 2209/088* (2013.01); *A61M 2210/101* (2013.01)

(58) Field of Classification Search
CPC .......... A61M 2025/0273; A61M 1/008; A61M 25/02; A61M 2025/028; A61M 2025/024; A61M 2025/0246; A61M 2005/1586; F16L 3/13; F16L 3/1025; F16L 3/1091
See application file for complete search history.

(56) References Cited

U.S. PATENT DOCUMENTS

| | | | | |
|---|---|---|---|---|
| 3,462,804 A | * | 8/1969 | Renaudin | F16L 3/10 248/74.4 |
| 4,397,647 A | * | 8/1983 | Gordon | A61M 25/02 128/DIG. 26 |
| 4,881,705 A | | 11/1989 | Kraus | |
| 5,029,782 A | * | 7/1991 | Andre | F16L 3/2235 248/68.1 |
| 5,184,794 A | | 2/1993 | Saito | |
| 5,693,032 A | | 12/1997 | Bierman | |
| 5,996,945 A | | 12/1999 | Coles et al. | |
| 6,213,979 B1 | | 4/2001 | Bierman | |

(Continued)

*Primary Examiner* — Adam Marcetich
(74) *Attorney, Agent, or Firm* — Faegre Drinker Biddle & Reath LLP

(57) ABSTRACT

A tube securing device is provided comprising: a base including a lower plate and a pair of inner walls, each of the inner walls including a ledge extending therefrom which forms a notch between the ledge and the lower plate, the base further including a groove between the inner walls sized to receive a tube in communication with a cavity of a patient; and a retainer including an upper plate and a pair of retention beams, each of the retention beams including a ridge extending therefrom, the retainer further including a groove between the retention beams sized to receive the tube. The tube is retained in the groove of the base and the groove of the retainer when the retainer is attached to the base by forcing the ridges over the ledges until the ridges snap into notches.

18 Claims, 12 Drawing Sheets

(56) References Cited

U.S. PATENT DOCUMENTS

| | | |
|---|---|---|
| 6,382,568 B1 | 5/2002 | Snell |
| 6,572,588 B1 | 6/2003 | Bierman et al. |
| 6,582,403 B1* | 6/2003 | Bierman ............... A61M 25/02 |
| | | 604/174 |
| 10,034,971 B2 | 7/2018 | Abu-Sultaneh et al. |
| 2006/0015072 A1 | 1/2006 | Raulerson |
| 2007/0142784 A1 | 6/2007 | Dikeman et al. |
| 2007/0142785 A1* | 6/2007 | Lundgaard ............. F16L 3/223 |
| | | 604/179 |
| 2008/0125718 A1* | 5/2008 | Tsuchiya ............... A61M 25/02 |
| | | 604/174 |
| 2009/0143742 A1 | 6/2009 | Bracken et al. |
| 2011/0118670 A1 | 5/2011 | Kay et al. |
| 2012/0009012 A1* | 1/2012 | Allenbach ............. F16L 3/237 |
| | | 403/344 |
| 2012/0217353 A1 | 8/2012 | Hennon |
| 2013/0018319 A1* | 1/2013 | Abe ..................... A61M 25/02 |
| | | 604/174 |
| 2013/0072875 A1* | 3/2013 | Rosenberg ............ A61M 25/02 |
| | | 604/174 |
| 2013/0079721 A1 | 3/2013 | Mizoguchi et al. |
| 2014/0163515 A1 | 6/2014 | Hyman et al. |
| 2014/0284432 A1* | 9/2014 | Shepard ................... F16L 3/11 |
| | | 248/74.2 |
| 2014/0324024 A1* | 10/2014 | Tejani .................. A61M 25/02 |
| | | 604/508 |
| 2015/0088075 A1* | 3/2015 | Khalaj .................. A61M 25/02 |
| | | 604/174 |
| 2015/0100025 A1* | 4/2015 | Rosenberg ............ A61M 25/02 |
| | | 604/174 |
| 2015/0141962 A1 | 5/2015 | Collins et al. |
| 2015/0192225 A1* | 7/2015 | Vo ........................... B23P 19/10 |
| | | 248/67.5 |
| 2016/0213322 A1* | 7/2016 | Goldberg ........... A61F 13/0226 |
| 2016/0334044 A1 | 11/2016 | Koenig |
| 2017/0122462 A1* | 5/2017 | Langenbacher .......... F16L 3/10 |
| 2017/0227141 A1* | 8/2017 | Toll ......................... F16L 3/237 |

* cited by examiner

TUBE SECURING DEVICE

RELATED APPLICATIONS

The present application is a continuation-in-part of U.S. patent application Ser. No. 14/860,030, filed Sep. 21, 2015, entitled "TUBE SECURING DEVICE," which is based on and claims priority to U.S. Provisional Application Ser. No. 62/053,328, filed Sep. 22, 2014, entitled "CHEST TUBE SECURING DEVICE," the entire disclosures of which being hereby incorporated herein by reference.

FIELD OF THE DISCLOSURE

The present disclosure is related to a device for securing tubes, such as chest tubes to a patient. The present disclosure is related more specifically to a tube securing device that is attached to a patient's body with an adhesive layer.

BACKGROUND

Chest tubes are flexible plastic tubes that are used to drain fluids or gases that have accumulated in the pleural space. Chest tube placement, known as tube thoracostomy, involves the following steps: administering a local anesthetic to the patient's chest, creating an incision between the patient's ribs, feeding a chest tube into the patient's pleural space, securing the chest tube, and allowing the fluid and /or gas to drain, with or without the assistance of suction. At present, the act of securing the chest tube is often accomplished by suturing the tube directly to the patient. This technique has several disadvantages. First, sutured chest tubes, especially smaller sized tubes, often become dislodged from patients. When a sutured tube dislodges, the patient can experience bleeding, pain, and even pneumothorax. Second, suturing takes a substantial amount of time. Suturing is disadvantageous in emergency situations, when time is of the essence. Third, suturing may limit the patient's movement because the chest tube is prone to dislodgment.

Accordingly, there exists the need for a device that can secure a chest tube to a patient without requiring health professionals to suture the tube in place.

SUMMARY

In one embodiment, the present disclosure provides a tube securing device comprising a base, a tube mount including a tube receptacle configured to receive a tube in communication with a cavity of a patient, a retainer, and at least one fastener mounted to one of the base and the retainer and configured to cooperate with the other of the base and the retainer to retain the tube mount between the base and the retainer. In one aspect of this embodiment, the device further comprises an adhesive strip attached to a lower wall of the base, the adhesive strip including a lower surface having an adhesive to attach the device to the patient. In another aspect, the base includes a groove sized to receive the tube receptacle of the tube mount. In a variant of this aspect, the groove includes a curved inner surface. In another aspect the tube receptacle has a cylindrical wall and defines an opening for receiving the tube. In a variant of this aspect, the opening of the tube receptacle is operable to receive tubes having outer diameters within the range of 6 Fr to 40 Fr. In still another aspect, the fastener is connected to an upper wall of the base. In a variant, the retainer includes a receptacle for receiving the fastener to thereby attach the retainer to the base and retain the tube mount between the base and the retainer. In a further variant, the tube mount includes a body having an opening that permits the fastener to extend through the body from the upper wall of the base to the receptacle of the retainer. In yet another aspect of this embodiment, the cylinder comprises rubber. In another aspect, the base and the retainer comprise polyvinyl chloride.

In another embodiment, the present disclosure provides a method of securing a tube to a patient comprising inserting the tube through an opening in a tube receptacle of a tube mount, placing the tube receptacle into a groove of a base, attaching a retainer to the base using at least one fastener, thereby retaining the tube mount between the base and the retainer, and adhering the base to the patient. In one aspect of this embodiment, adhering includes attaching an adhesive strip to a lower wall of the base. In another aspect, inserting includes placing one end of the tube through a longitudinal opening extending through the tube receptacle. In yet another aspect, inserting includes opening a side wall of the tube receptacle and passing a portion of the tube through the side wall opening into the opening of the tube receptacle. In yet another aspect of this embodiment, attaching includes passing a pair of fasteners connected to a top wall of the base through openings in a body of the tube mount and into a pair of receptacles formed in the retainer. In another aspect, the base and the retainer are formed of PVC and the tube receptacle is formed of rubber. In yet another aspect, the tube receptacle is cylindrical in cross-section and the groove is sized to receive the tube receptacle. In a further aspect, the tube receptacle is sized to receive chest tubes within one of the ranges of 16 Fr to 22 Fr and 28 Fr to 36 Fr.

In yet another embodiment of the present disclosure, a chest tube securing device is provided comprising a base having a top wall, a bottom wall, a front wall, a rear wall, a plurality of fasteners extending from the top wall, and a groove formed into the top wall and extending between the front wall and the rear wall, a tube mount including a body having a plurality of openings and a tube receptacle configured to receive a tube in communication with a chest cavity of a patient, the tube receptacle being sized to be received by the groove in the top wall of the base, a retainer having a top wall, a bottom wall, and a plurality of receptacles extending into the retainer from the bottom wall, the plurality of receptacles being aligned with the plurality of openings in the tube mount body and the plurality of fasteners to receive the fasteners and retain the tube mount between the base and the retainer, and an adhesive strip attached to the bottom wall of the base and having a lower surface with an adhesive to attach the chest tube securing device to the patient.

In still another embodiment, a tube securing device is provided comprising: a base including a lower plate and a pair of inner walls, each of the inner walls including a ledge extending therefrom which forms a notch between the ledge and the lower plate, the base further including a groove between the inner walls sized to receive a tube in communication with a cavity of a patient; and a retainer including an upper plate and a pair of retention beams, each of the retention beams including a ridge extending therefrom, the retainer further including a groove between the retention beams sized to receive the tube; wherein the tube is retained in the groove of the base and the groove of the retainer when the retainer is attached to the base by forcing the ridges over the ledges until the ridges snap into notches. One aspect of this embodiment further comprises an adhesive layer attached to the lower plate of the base, the adhesive layer including an adhesive to adhere the adhesive layer to the patient. Another aspect further comprises a tube receptacle having a first portion disposed within a recess formed in the base and a second portion disposed in a recess formed in the retainer, the groove of the base being formed in the first portion and the groove of the retainer being formed in the second portion. In a variant of this aspect, the first portion of the tube receptacle extends between a first end of the base and a second end of the base and the second portion of the tube receptacle extends between a first end of the retainer and a second end of the retainer. In another variant, the tube receptacle is formed from a first material and the base and the retainer are formed from a second material. In still a further aspect, the first material is a rubber-like thermoplastic and the second material is a hard photopolymer. In another aspect of this embodiment, at least one of the groove of the base or the groove of the retainer includes at least one gripping feature. In another aspect, the lower plate of the base and the upper plate of the retainer form a pair of gaps between the base and the retainer when the retainer is attached to the base, the pair of gaps being configured to permit application of force to separate the retainer from the base.

In still another embodiment, the present disclosure provides a method of securing a tube to a patient, comprising: placing the tube into a groove formed in a first component of a tube securing device; placing a second component of the tube securing device onto the tube such that the tube is received by a groove in the second component; applying a force to at least one of the first component and the second component to move the first component and the second component toward one another, thereby causing a pair of ridges of one of the first component or the second component to snap into a corresponding pair of notches of the other of the first component or the second component to connect the first component and the second component; and adhering one of the first component or the second component to the patient. One aspect of this embodiment further comprises inserting a first portion of a tube receptacle into a recess in the first component, the first portion including the groove of the first component; and inserting a second portion of a tube receptacle into a recess in the second component, the second portion including the groove of the second component. In a variant of this aspect, the first portion of the tube receptacle extends between a first end of the first component and a second end of the first component and the second portion of the tube receptacle extends between a first end of the second component and a second end of the second component. In another variant, the tube receptacle is formed from a first material and the first and second components are formed from a second material. In a further variant, the first material is a rubber-like thermoplastic and the second material is a hard photopolymer. In still another aspect of this embodiment, the first component includes a lower plate and a pair of inner walls, each of the inner walls including a ledge extending therefrom which forms one of the notches between the ledge and the lower plate, and the second component includes an upper plate and a pair of retention beams, each retention beam including one of the ridges. In a variant of this aspect, the groove of the first component is formed between the inner walls and the groove of the second component is formed between the retention beams. In another variant, the lower plate of the first component and the upper plate of the second component form a pair of gaps between the first component and the second component when the first component is connected to the second component, the pair of gaps being configured to permit application of force to separate the first component from the second component. In still another aspect of this embodiment, at least one of the groove of the first component or the groove of the second component includes at least one gripping feature.

In yet another embodiment, the present disclosure provides a chest tube securing device comprising: a base having a lower plate and a pair of inner walls extending from the lower plate and between a pair of end walls of the base, the base including a groove disposed between the inner walls and extending between the pair of end walls; a retainer having an upper plate and a pair of retention beams extending from the upper plate, the retainer including a groove disposed between the retention beams and extending between a pair of end surfaces of the retainer; and an adhesive layer attached to a lower surface of the lower plate and having a lower surface with an adhesive layer; wherein the tube is received within an opening formed by a groove in the base extending between the end walls and the groove in the retainer and secured in the chest tube securing device by mating engagement between a pair of notches formed by ledges extending from the inner walls of the base and a pair of ridges extending from the retention beams of the retainer. One aspect of this embodiment further comprises a tube receptacle having a first portion disposed within a recess formed in the base and a second portion disposed in a recess formed in the retainer, the groove of the base being formed in the first portion and the groove of the retainer being formed in the second portion. In a variant of this aspect, the tube receptacle is formed from a first material and the base and the retainer are formed from a second material.

BRIEF DESCRIPTION OF THE DRAWINGS

The above-mentioned aspects of the present teachings and the manner of obtaining them will become more apparent and the teachings will be better understood by reference to the following description of the embodiments taken in conjunction with the accompanying drawings, wherein.

Corresponding reference characters indicate corresponding parts throughout the several views.

DETAILED DESCRIPTION OF THE DRAWINGS

The embodiments disclosed herein are not intended to be exhaustive or to limit the disclosure to the precise forms disclosed in the following detailed description. Rather, the embodiments were chosen and described so that others skilled in the art may utilize their teachings.

Figure 1:
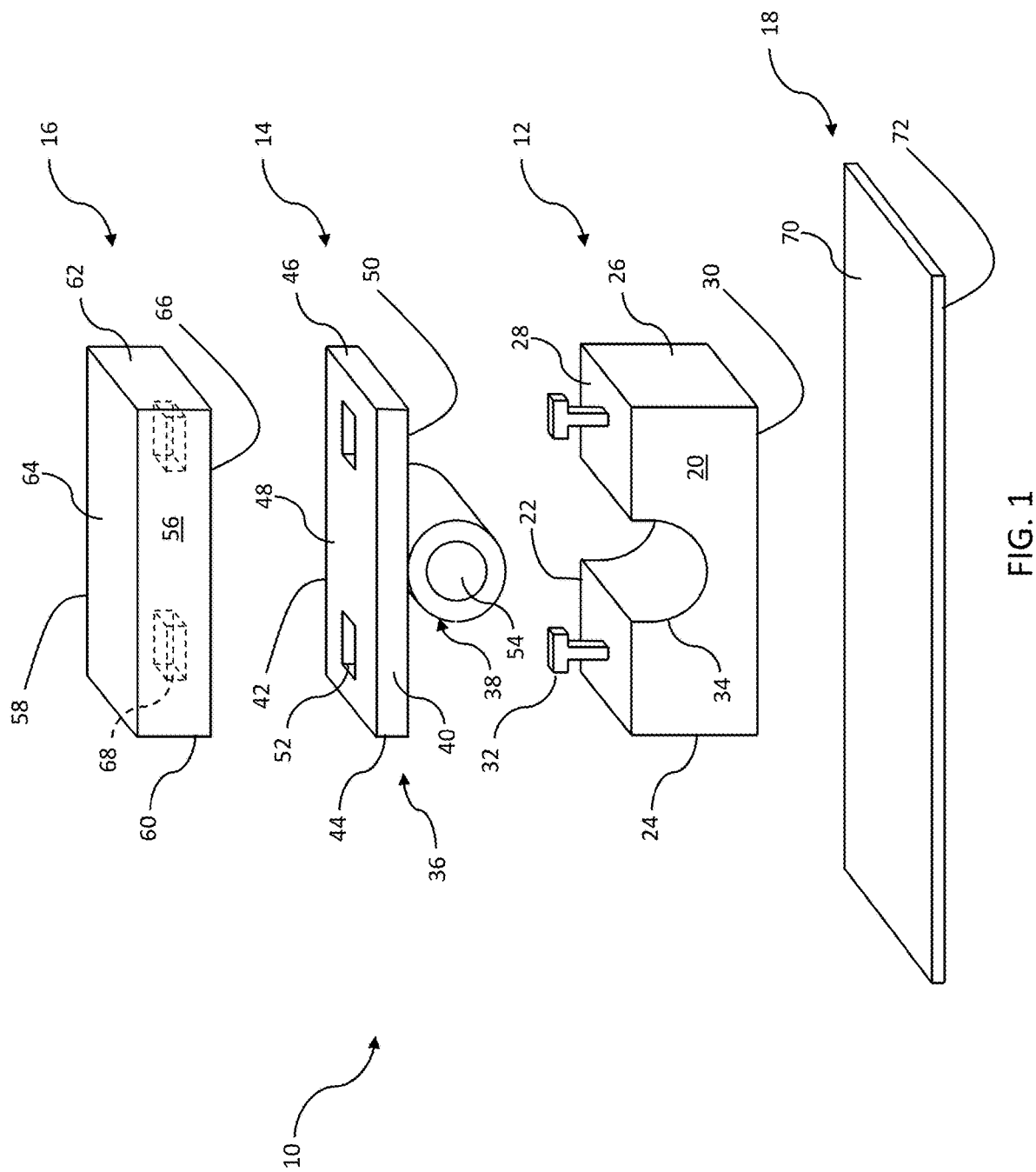
FIG. 1 is a perspective view illustrating components of one embodiment of a tube securing device according to the principles of the present disclosure.

A first representative embodiment of the present disclosure is shown in FIG. 1. As shown, an exemplary tube securing device 10 generally includes a base 12, a tube mount 14, a retainer 16 and an adhesive strip 18. While portions of this disclosure describe the tube securing device 10 in the context of securing chest tubes, it should be understood that device 10 may have many other tube securing applications, all of which are intended to be within the scope of the present disclosure. In one embodiment, base 12 includes a front wall 20, a rear wall 22, side walls 24, 26, a top wall 28, a bottom wall 30 and fasteners 32. Base 12 further includes a recess or groove 34 that extends from front wall 20 to rear wall 22 and is opened to top wall 28. Groove 34 is sized to approximate the diameter of a component of tube mount 14 as is further described below.

Fasteners 32 are depicted as being male fasteners of a particular shape, and later described as cooperating with female receptacles of retainer 16 for securing tube mount 14 within device 10. As will be apparent to those skilled in the art, however, fasteners 32 may have any of a variety of suitable shapes, be located at various locations of base 12, or be located on retainer 16. In other words, fasteners 32 need not be T-shaped, but may be formed to resemble a hook, a prong, a stud, an L-shape, etc. Fasteners 32 need not be mounted to top wall 28 of base 12, but may be connected to one or more of side walls 24, 26, front wall 20, rear wall 22, etc. Moreover, fasteners 32 may be connected to retainer 16, and base 12 may include female receptacles to cooperate with fasteners 32 to secure tube mount 14 within device 10. Additionally, fasteners 32 may be snaps, Velcro®, toggle latches, catch bolts, toggle clamps, removable elastic bands or straps or any other structure that provides cooperation between base 12 and retainer 16 to secure tube mount 14 between base 12 and retainer 16.

In one application, tube securing device 10 is operable to secure a chest tube to a patient's person without the use of sutures. As such, device 10 may lower the risk of chest tube dislodgement, especially when using small chest tubes, enhance patient mobility, and lower the amount of time needed to secure chest tubes.

In the depicted embodiment, tube mount 14 generally includes a body 36 and a tube receptacle 38. Body 36 includes a front wall 40, a rear wall 42, side walls 44, 46, a top wall 48, and a bottom wall 50. In certain embodiments, body 36 further includes openings 52 for receiving fasteners 32 in the manner described below. Body 36 is depicted as being generally plate shaped and having lateral dimensions that generally approximate the lateral dimensions of base 12. It should be understood, however, that body 36 may have any of a variety of different shapes and dimensions, and is intended to provide a structure to attach to tube receptacle 38 and permit tube receptacle 38 to be secured to device 10.

Tube receptacle 38 is shown mounted or attached to bottom wall 50 of body 36. It should be understood, however, that tube 38 and body 36 may be formed as one piece or more than two pieces. Tube receptacle 38 is depicted as being cylindrical in shape, and having a central opening 54 with a diameter sufficient to receive a tube (e.g., a chest tube). Tube receptacle 38 may, however, be non-cylindrical in shape. Additionally, tube receptacle 38 may have a longitudinal slit or gap (not shown) that permits a side of receptacle 38 to be opened for receiving a tube into opening 54 laterally, rather than through an end of receptacle 38. Body 36 and tube receptacle 38 may be formed of resilient materials such as rubber or other material. Rubber may be a particularly advantageous material because it is widely available, flexible, and forms a very tight fit with PVC (a material suitable for base 12 and retainer 16). As used in tube receptacle 38, rubber may serve the dual purpose of securing a tube and preventing receptacle 38 from moving within groove 34 of base 12.

Retainer 16 includes a front wall 56, a rear wall 58, side walls 60, 62, a top wall 64, a bottom wall 66 and receptacles 68. As explained above, retainer 16 may include fasteners 32 instead of receptacles 68. Retainer 16 is depicted as being generally plate shaped and having lateral dimensions that generally approximate the lateral dimensions of body 36 of tube mount 14 and base 12. It should be understood, however, that retainer 16 may have any of a variety of different shapes and dimensions, and is intended to provide a structure that cooperates with base 12 to secure tube mount 14 to device 10.

Finally, adhesive strip 18 generally includes an upper surface 70 and a lower surface 72. Upper surface 70 and/or lower surface 72 may include a pressure sensitive adhesive (PSA), which is a viscoelastic adhesive material that requires a light amount of pressure, such as pressing down, in order to adhere to a surface. PSAs are a common class of medical adhesives because they typically adhere to human skin without greatly damaging the skin when removed. Examples of PSAs include, but are not limited to, silicone adhesives, acrylic adhesives, polyolefins, polyurethane, synthetic rubber, and natural rubber. In a more particular embodiment, adhesive strip 18 is coated on upper surface 70 and lower surface 72 with a PSA. In another embodiment, only lower surface 72 (i.e., the surface that interacts with the patient's skin) is coated with a PSA. In other embodiments, adhesive strip 18 is coated with a non-PSA adhesive material, such as an epoxy or a cyanoacrylate adhesive. In some embodiments, adhesive strip 18 is a tape made of paper, cloth, or a synthetic solid material, such as silicone, that is coated with a PSA. Generally, upper surface 70 of adhesive strip 18 is attached to lower wall 30 of base 12 ad lower surface 70 of adhesive strip 18 is attached to the patient's skin.

Figure 2:
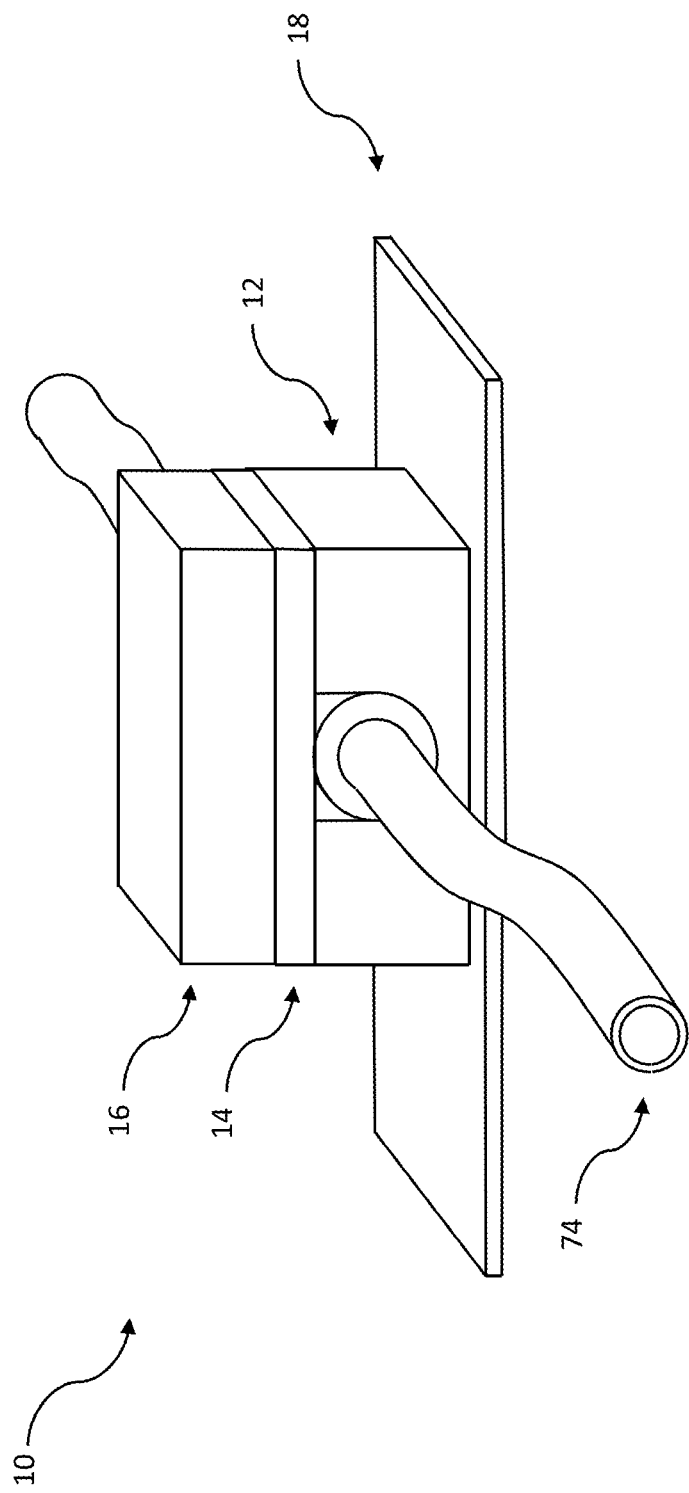
FIG. 2 is a perspective view of the device of FIG. 1 in a fully assembled state.

A fully assembled tube securing device 10 securing a tube 74 (such as a chest tube) is depicted in FIG. 2.

In one embodiment of the present disclosure, tube securing device 10 is used in the following manner. Tube 74 (such as a chest tube) is first passed through opening 54 of tube receptacle 38. The interior diameter of opening 54 may be sized to accommodate a wide range of chest tube sizes. Smaller size chest tubes, for example, within the range of 16 Fr to 22 Fr or 6 Fr to 8.5 Fr for pediatric patients, are typically used to treat pneumothorax. Small sized chest tubes are suitable for pneumothorax because pleural gas can easily pass through smaller tubes. Additionally, small bore chest tubes are typically easier to insert and cause less pain to the patient. In circumstances where the patient is suffering from a pleural effusion, for example hemothorax or empyema, a larger sized chest tube must typically be used to remove the fluid. A typical chest tube size employed when treating a pleural effusion ranges from 28 Fr to 36 Fr, although smaller tube may also be used in certain applications. These size ranges are illustrative and can shift depending on the body size of the patient. For example, a pediatric patient will often require a much smaller chest tube size than an adult patient. It should be understood that tube securing devices 10 having different dimensions to accommodate different size chest tubes may be manufactured and made available to health care providers.

After tube 74 is positioned within opening 54, tube mount 14 is placed onto base 12 such that tube receptacle 38 is situated within groove 34. In certain embodiments, such placement of tube mount 14 causes openings 52 of tube mount body 36 to pass over fasteners 32 of base 12 such that fasteners 32 protrude through openings 52 for connection to receptacles 68 of retainer 16. In one exemplary embodiment, base 12 is a rectangular body of polyvinyl chloride (PVC). Retainer 16 may also be formed of PVC. In one exemplary embodiment, rubber padding (not shown) is coupled to the curved inner surface of groove 34.

Next, retainer 16 is placed onto tube mount body 36 such that receptacles 68 of retainer 16 engage fasteners 32 of base 12 to retain tube mount 14 in place. In certain embodiments, retainer 16 may apply a compressive force to body 36 when attached to fasteners 32. Finally, adhesive strip 18 is attached to lower wall 30 of base 12. It should be understood, however, that adhesive strip 18 may be attached to base 12 before, during or after the above-described assembly of the other components of device 10.

Figure 3:
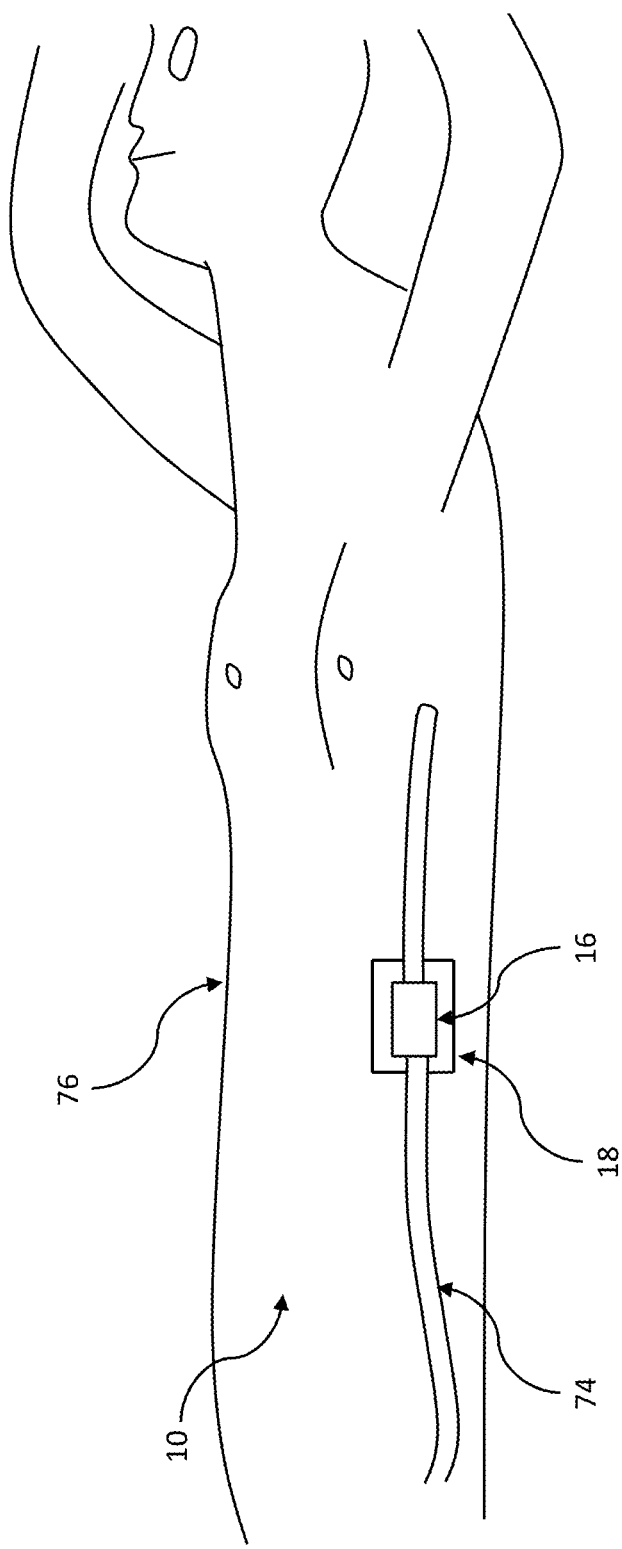
FIG. 3 illustrates one embodiment of a fully assembled tube securing device attached to a supine patient.

FIG. 3 illustrates a completed tube securing device 10 on the chest of supine patient 76 functioning to secure a chest tube 74. In this illustration, chest tube 74 is secured by tube securing device 10, and chest tube 74 has been positioned into supine patient 76's pleural space. Typically, chest tube 74 will be placed into the patient's pleural space before tube securing device 10 is coupled to supine patient 76.

Figure 4:
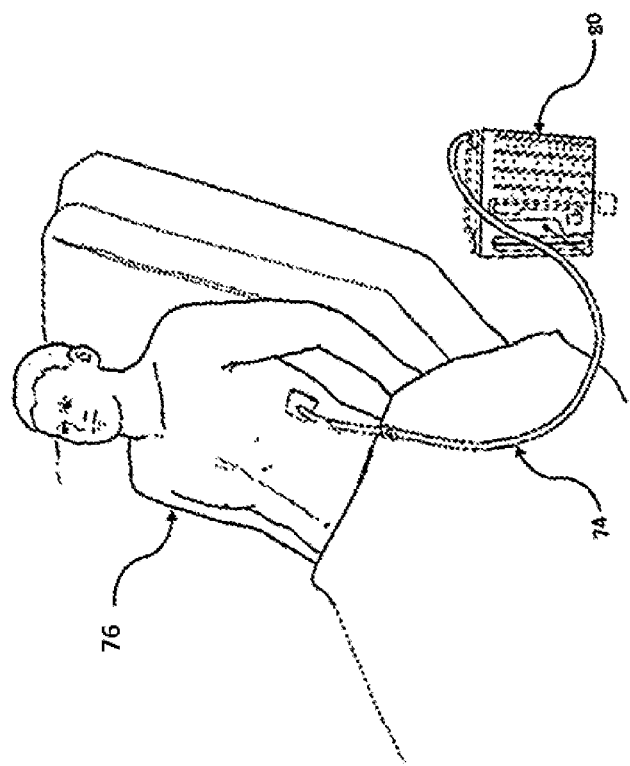
FIG. 4 illustrates another embodiment of a fully assembled tube securing device attached to a patient.

FIG. 4 provides another view of a chest tube 74 connected to a patient 76. As indicated above, chest tubes are flexible plastic tubes that are used to drain fluids or gases that have accumulated in the pleural space, which is the space between the lungs and rib cage. Chest tube placement is routinely performed by intensive care physicians, interventional radiologists and by surgeons at children's and adult hospitals. Precise statistics on how many chest tubes are placed in the United States each year are not available, but it is estimated that approximately 1.5 million people per year develop pleural effusion in the United States. Each year, at least 200 pigtail chest tubes are being placed at The Riley Hospital for Children—one of 210 children's hospitals in the United States.

Chest tube placement, known as tube thoracostomy, involves the following steps: (1) administering a local anesthetic to the patient's chest, (2) creating an incision between the patient's ribs, (3) feeding a chest tube into the patient's pleural space, (4) securing the chest tube, and (5) allowing the fluid and/or gas to drain, with or without the assistance of suction from a drainage device 80 as shown in FIG. 4. In conventional approaches, the act of securing the chest tube is often accomplished by suturing the tube directly to the patient's chest. However, this technique has several disadvantages. First, sutured chest tubes, especially smaller sized tubes, often become dislodged from patients. When a sutured tube dislodges, the patient can experience bleeding, pain, and even pneumothorax (i.e., an accumulation of air in pleural space). Second, suturing takes a substantial amount of time. Suturing is especially disadvantageous in emergency situations, when time is of the essence. Third, suturing may limit the patient's movement because the chest tube is prone to dislodgment. Fourth, using suturing puts the physician at risk for needle-stick injury.

Figure 5:
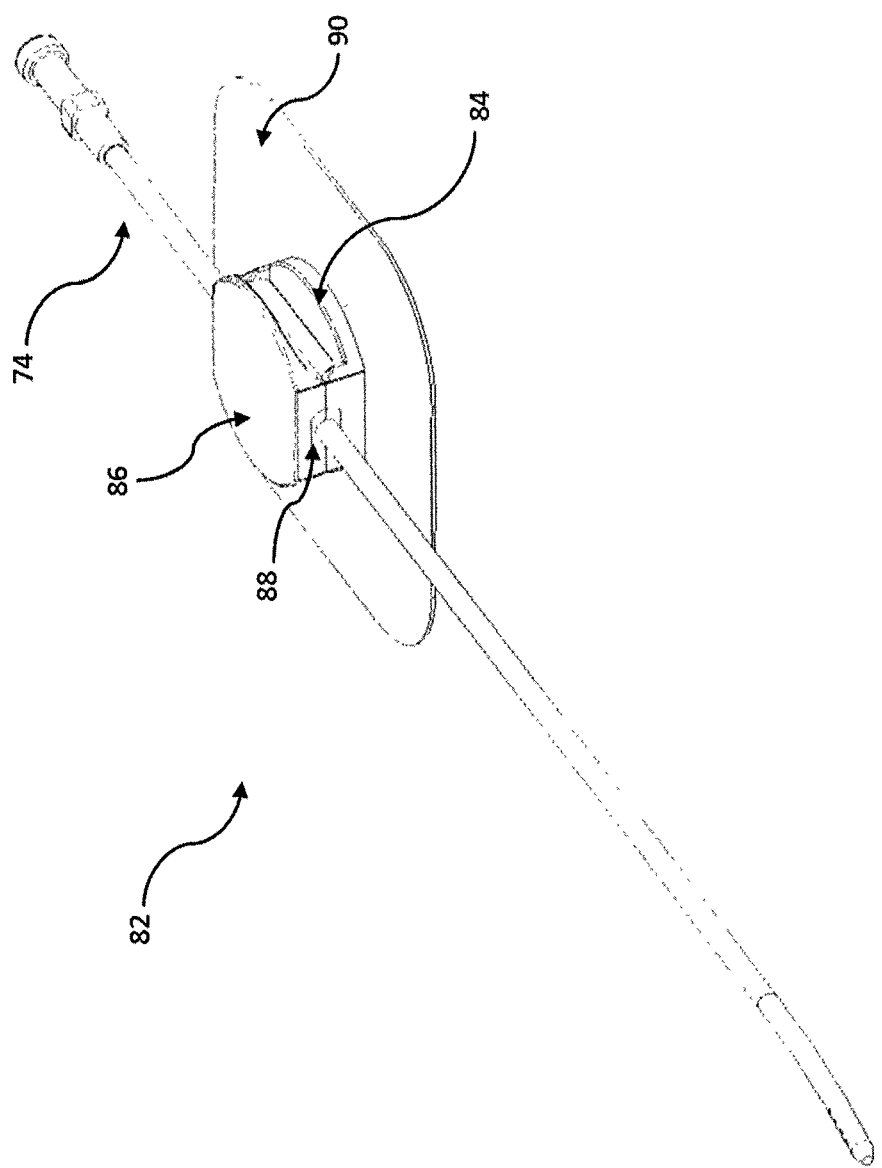
FIG. 5 is a perspective view of the device of FIG. 4.

To address the disadvantages of the current suturing practice, the chest tube securing devices of the present disclosure are provided such that they may be used to secure the chest tube to the patient's chest wall without the need of sutures. Another embodiment of a tube securing device according to the present disclosure is shown in FIGS. 5-10. As shown in FIG. 5, device 82 generally includes a base 84, a retainer 86, a tube receptacle 88 and an adhesive layer 90.

As is generally shown, tube 74 extends through and is held in place by device 82, which is attached to the patient by adhesive layer 90.

Figure 6:
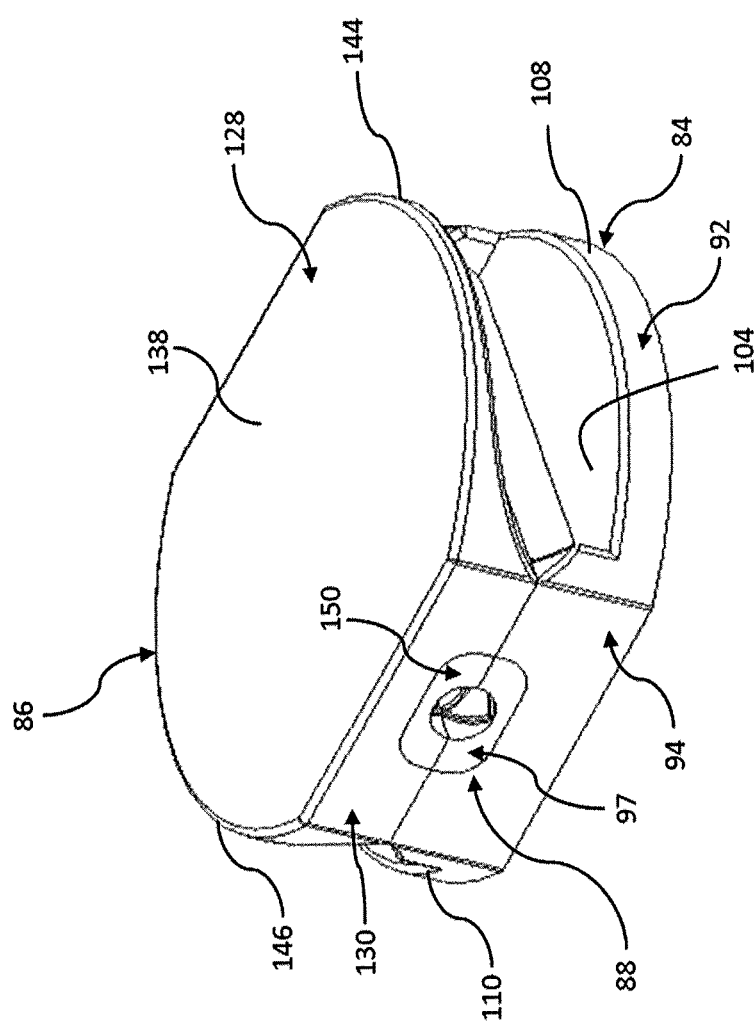
FIG. 6 is another perspective view of the device of FIG. 4.
Figure 7:
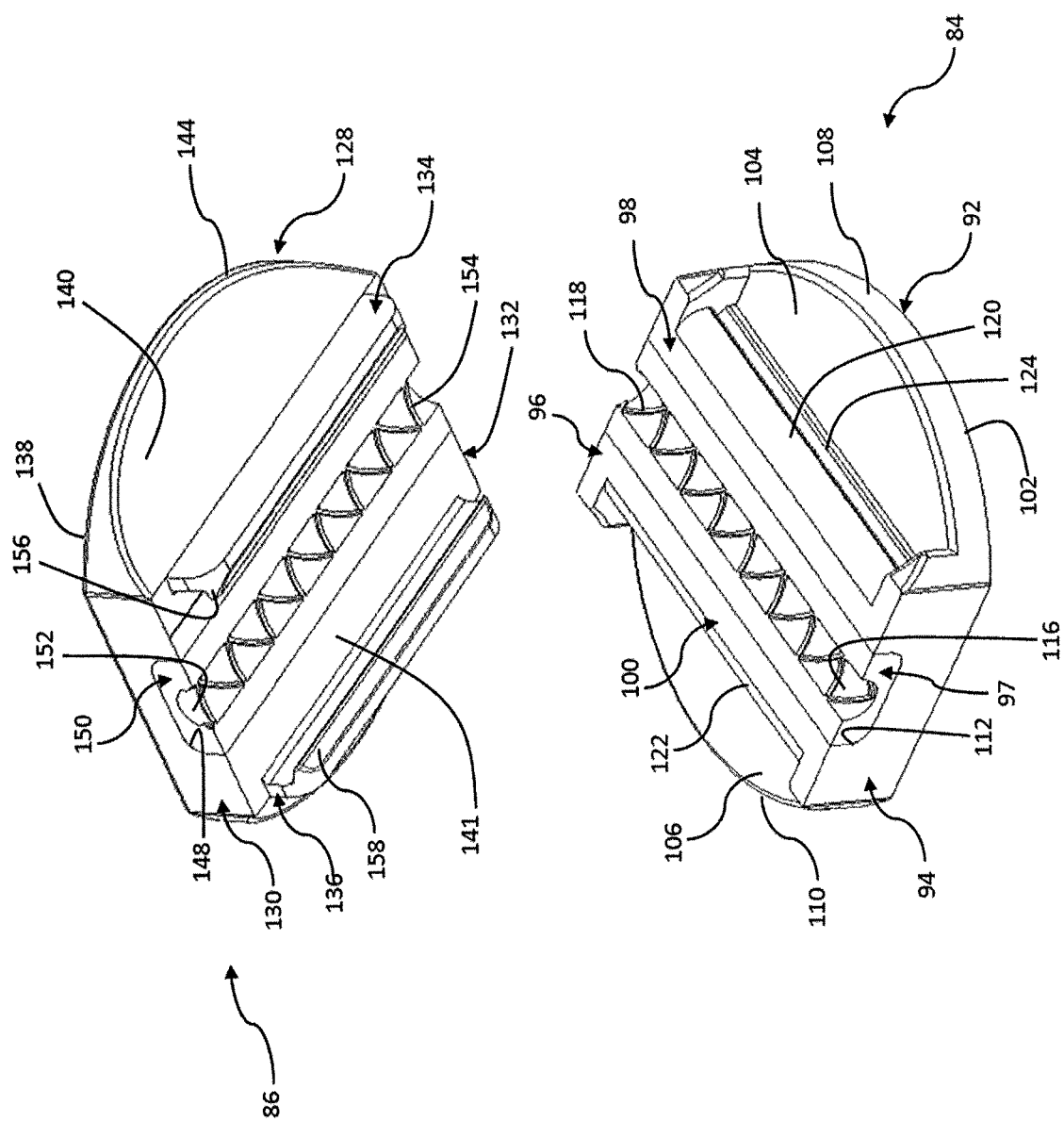
FIG. 7 is a perspective view of the device of FIG. 4 in a disassembled state.
Figure 8:
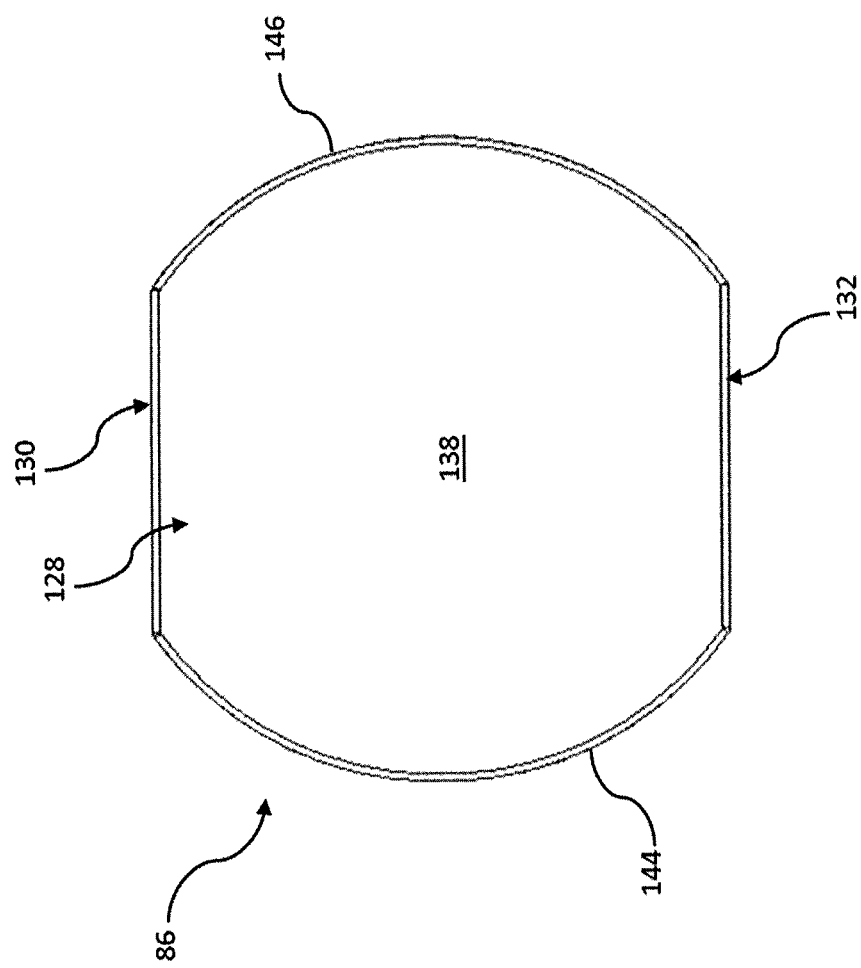
FIG. 8 is a top view of the device of FIG. 4.

As best shown in FIGS. 6-8, base 84 generally includes a lower plate 92, a pair of end walls 94, 96, and a pair of inner walls 98, 100 extending between end walls 94, 96 and lower plate 92. Lower plate 92 has a flat lower surface 102 configured to engage adhesive layer 90 to secure adhesive layer 90 to base 84. Lower plate 92 further includes an upper surface 104 adjacent inner wall 98 and an upper surface 106 adjacent inner wall 100. Lower plate 92 includes a first curved edge 108 connecting lower surface 102 and upper surface 104 and extending between end walls 94, 96, and a second curved edge 110 connecting lower surface 102 and upper surface 106 and extending between end walls 94, 96.

End walls 94, 96 and inner walls 98, 100 define a recess 112 that extends the length of base 84 between end wall 94 and end wall 96. A first portion 97 of tube receptacle 88 is disposed within recess 112 and defines a groove 116 sized to receive tube 74 (FIG. 5). A plurality of gripping features 118 are formed in groove 116. Gripping features 118, in one embodiment, are indentations into groove 116 and in alternative embodiments are ridges or protrusions extending from groove 116. In any case, gripping features 118 are configured to provide increased friction between groove 116 and tube 74 as is further explained herein.

A ledge 120 extends from an upper end of inner wall 98 toward edge 108 of lower plate 92. A similar ledge 122 extends from an upper end of inner wall 100 toward edge 110 of lower plate 92. Ledge 120, inner wall 98 and upper surface 104 of lower plate 92 form a notch 124 that undercuts ledge 120. Similarly, ledge 122, inner wall 100 and upper surface 106 of lower plate 92 form a notch 126 (not shown) that undercuts ledge 122. The notches 124, 126 are configured to receive corresponding structure of retainer 86 to retain tube 74 within device 82 as is further described below.

Still referring to FIGS. 6-8, retainer 86 generally includes an upper plate 128, a pair of end surfaces 130, 132, and a pair of retention beams 134, 136. Upper plate 128 has a flat upper surface 138, a lower surface 140 adjacent retention beam 134, a lower surface 141 between beams 134, 136 and a lower surface 142 (not shown) adjacent retention beam 136. Upper plate 128 includes a first curved edge 144 connecting upper surface 138 and lower surface 140 and extending between end surfaces 130, 132, and a second curved edge 146 (FIG. 6) connecting upper surface 138 and lower surface 142 (FIG. 9) and extending between end surfaces 130, 132.

A recess 148 is formed into lower surface 141 that extends the length of retainer 86 between end surface 130 and end surface 132. A second portion 150 of tube receptacle 88 is disposed within recess 148 and defines a groove 152 sized to receive tube 74 (FIG. 5). A plurality of gripping features 154 are formed in groove 152. Gripping features 154, in one embodiment, are indentations into groove 152 and in alternative embodiments are ridges or protrusions extending from groove 152. In any case, gripping features 152 are configured to provide increased friction between groove 152 and tube 74 as is further explained herein.

A ridge 156 extends from a lower end of retention beam 134 away from edge 144 of upper plate 128. A similar ridge 158 extends from a lower end of retention beam 136 away from edge 146 of upper plate 128. Ridge 156 is positioned and sized to snap into notch 124 and ridge 158 is positioned and sized to snap into notch 126 when retainer 86 is attached to base 84.

Figure 9:
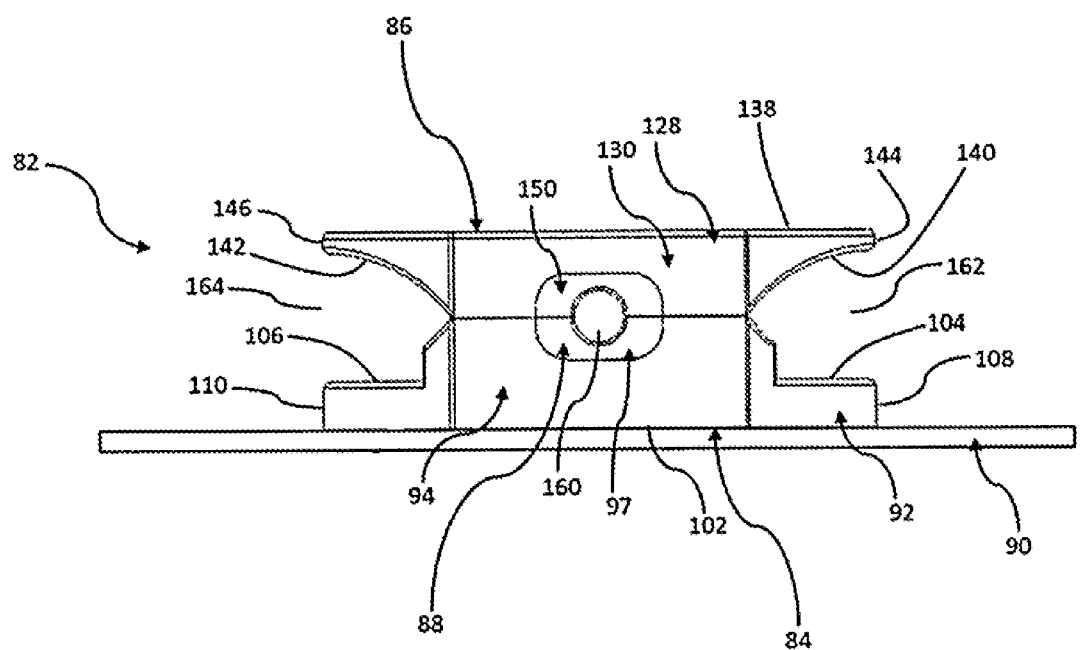
FIG. 9 is an end view of the device of FIG. 4.

Referring now to FIG. 9, base 84 and retainer 86 form an opening 160 for receiving tube 74. Additionally, upper surface 104 of base 84 and lower surface 140 of retainer 86 for a gap 162 and upper surface 106 of base 84 and lower surface 142 of retainer 86 form a gap 164.

In use, adhesive layer 90 is attached to the skin of the patient. Tube 74 is positioned within first portion 97 of tube receptacle 88, and then retainer 86 is placed over base 84 and tube 74 such that tube 74 is received into second portion 150 of tube receptacle 88. Force is then applied to lower surface 102 of base 84 and upper surface 138 of retainer 86 to cause ridges 156, 158 to cam over ledges 120, 122, respectively, and snap into notches 124, 126, respectively. It should be understood that retention beams 134, 136 are structured to be somewhat resilient such that they may bend away from one another as ridges 156, 158 cam over ledges 120, 122, and then return to substantially their original position relative to retainer 86 when ridges 156, 158 snap into notches 124, 126. When retainer 86 is attached to base 84, tube 74 is compressed within opening 160 formed by grooves 112, 148 and is retained in place in cooperation with gripping features 118, 154. The assembly of base 84, tube 74 and retainer 86 is then placed onto adhesive layer 90 such that lower surface 102 of base 84 adheres to adhesive layer 90, thereby securing tube 74 is a desired position.

To remove tube 74 from device 82, a caregiver places his or her fingers within gaps 162, 164 and applies force to urge retainer 86 away from base 84. The force causes ridges 156, 158 to withdraw from notches 124, 126, respectively, which releases retainer 86 from base 84. Tube 74 may then be removed.

While device 82 is described herein as including four primary components—adhesive layer 90, base 84, retainer 86 and tube receptacle 88, it should be understood that device 82 may include more or fewer components. For example, adhesive layer 90 may be integral with base 84. Additionally, tube receptacle 88 may be integral with base 84 and retainer 86. In other words, while tube receptacle 88 has been described as including a first portion 97 and a second portion 150 that are separate from base 84 and receptacle 86, it should be understood that base 84 may be formed to include first portion 97 and retainer 86 may be formed to include second portion 150.

Two versions of device 82 were tested to determine the degree to which they retain tube 74 in place. The first version (hereinafter "device 82A") included only two components (ignoring adhesive layer 90), which were both formed of a hard photopolymer (e.g., Tough Resin RS-F2-TOTL-05). In other words, in device 82A tube retainer 88 was integral with base 84 and retainer 86, and along with base 84 and retainer 86 was formed of hard photopolymer. The second version (hereinafter "device 82B") included three components (ignoring adhesive layer 90). Base 84 and retainer 86 were formed of hard photopolymer and tube receptacle 88 was formed of a rubber-like thermoplastic (e.g., Flexible Resin RS-F2-FLGR -02) and attached to base 84 and retainer 86 in the manner described above.

Devices 82A and 82B were mechanically tested for holding capacity (i.e., the extent to which tube 74 is retained within opening 160) using a universal testing machine (i.e., the Instron 5940) in a manner known in the art. A load was applied to tube 74 in a direction to pull tube 74 along its axis away from devices 82A, 82B while tube 74 was retained within the devices. An additional, commercially available tube retention device (i.e., the SecurAcath® device manufactured by Interrad Medical Inc. of Plymouth, Minn.) was also tested for comparison of devices 82A, 82B to a current system for securing central venous catheters.

Figure 10:
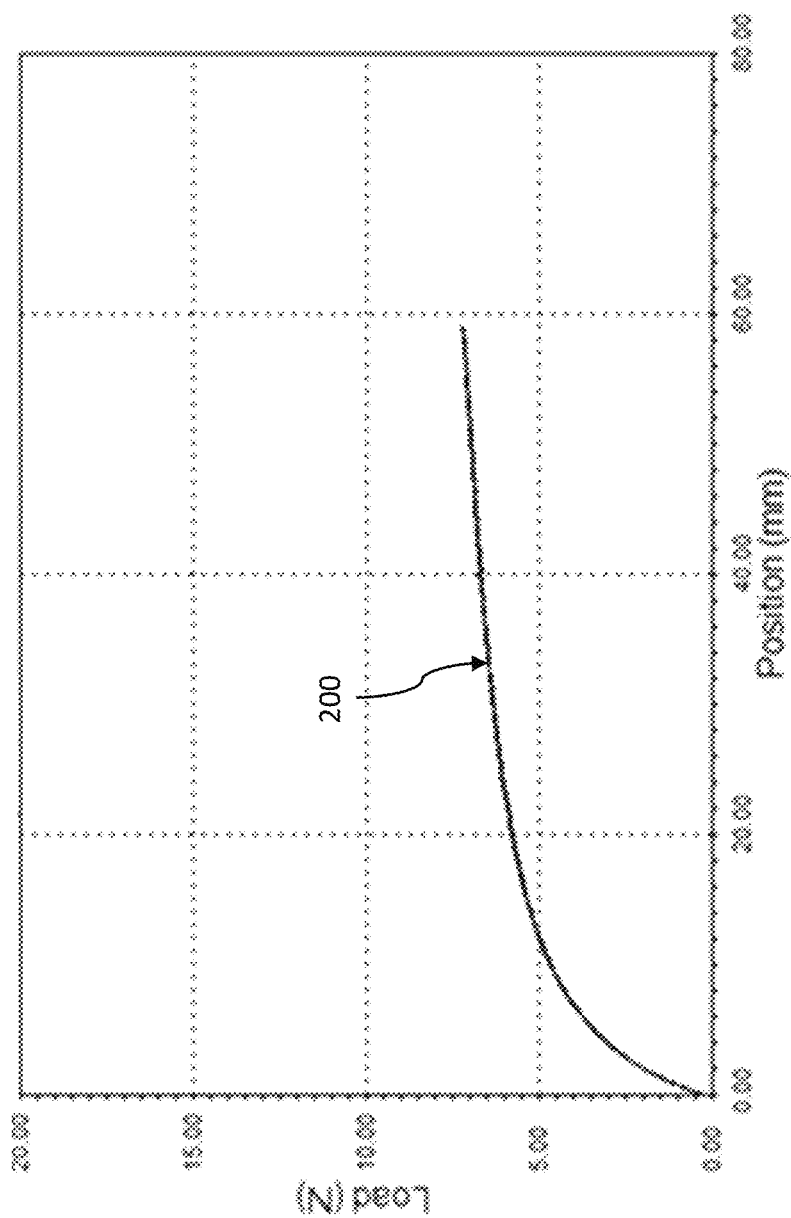
FIGS. 10-12 are graphs of retention test results of various tube securing devices.

Referring to FIG. 10, the test results for the SecurAcath® device are shown as measurement trace 200. As shown, during the first portion of trace 200 (i.e., from zero to approximately 14 mm), as the load on tube 74 was increased, tube 74 stretched (i.e., remained retained within the device). After tube 74 had stretched approximately 14 mm, it began to slip out of the SecurAcath® device, and the distance from the starting location of the tube 74 in the device increased greatly in response to increases in load above approximately 5 Newtons. Thus, the SecurAcath® device could retain tube 74 until a pulling load of approximately 5 or 6 Newtons was applied.

Figure 11:
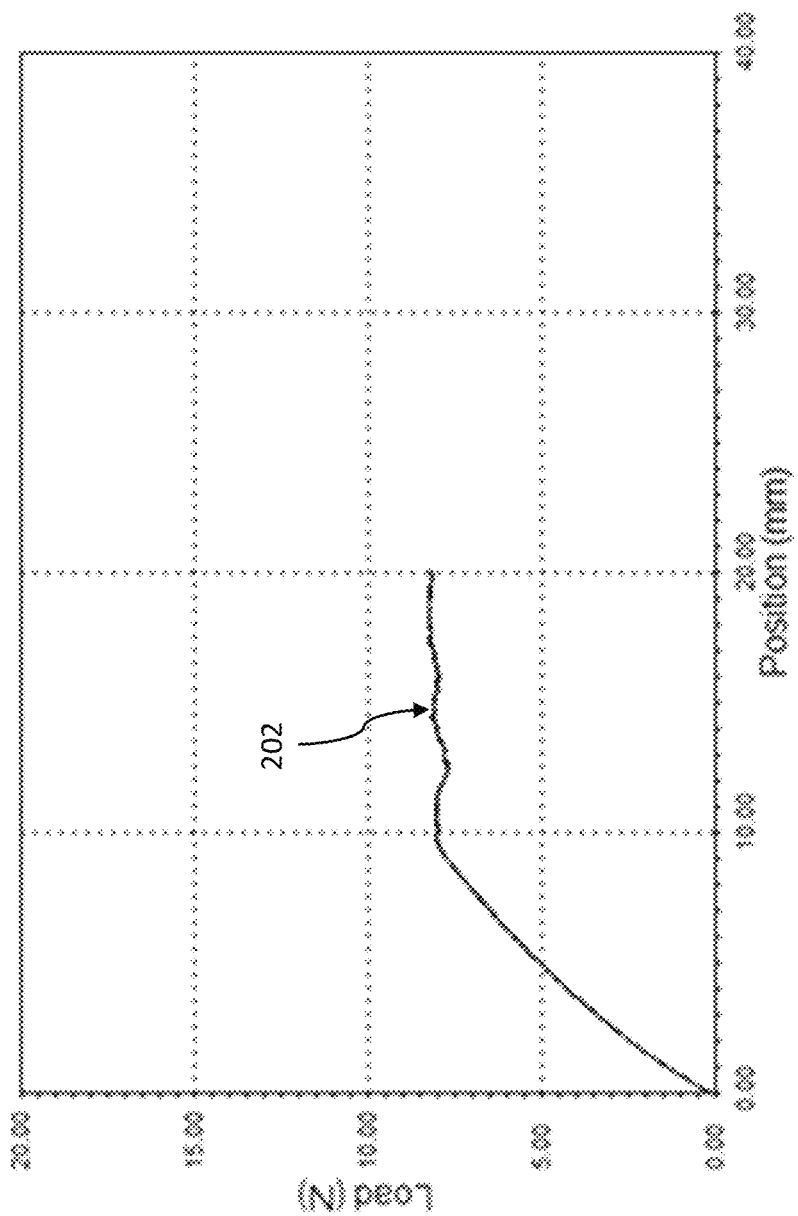

Referring to FIG. 11, the test results for device 82A are shown as measurement trace 202. As shown, during the first portion of trace 202 (i.e., from zero to approximately 10 mm), as the load on tube 74 was increased to approximately 8 Newtons the tube 74 stretched. After the tube had stretch approximately 10 mm, it began to slip out of device 82A. Thus, device 82A could retain tube 74 until a pulling load of approximately 8 Newtons was applied, which is better performance than the SecurAcath® device.

Figure 12:
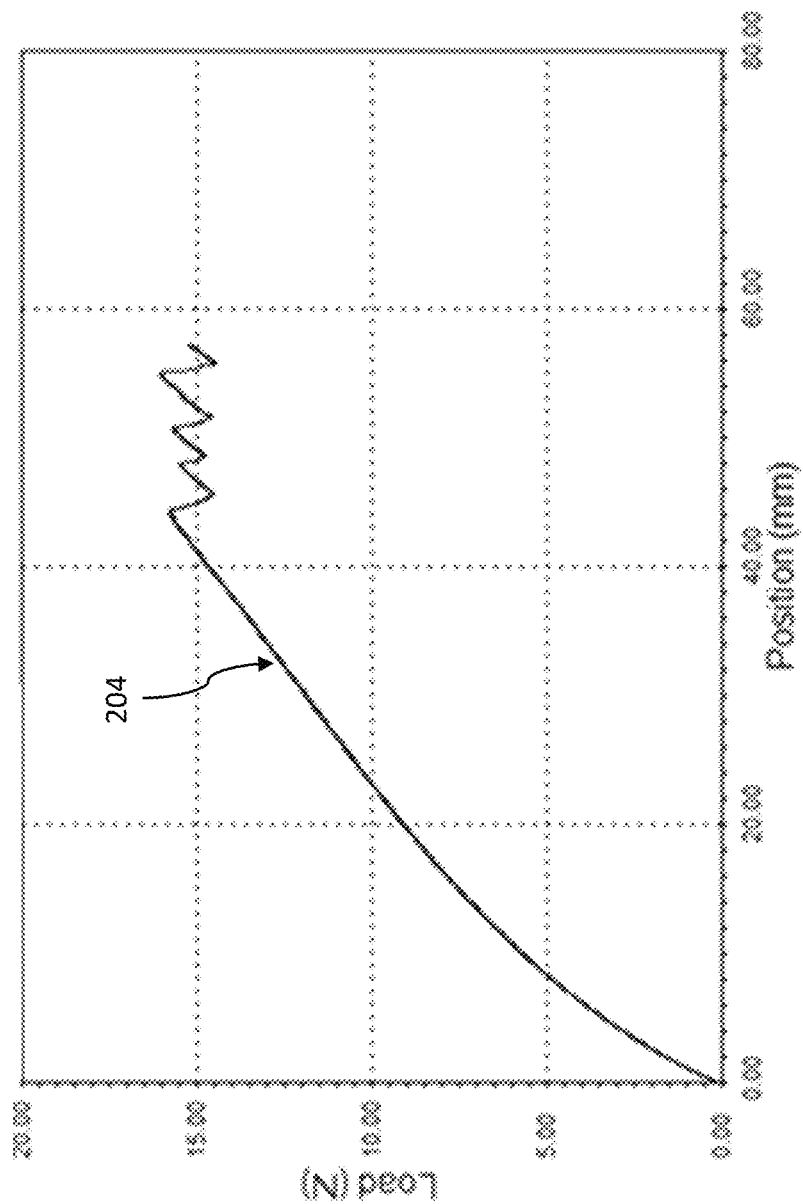

Referring now to FIG. 12, the test results for device 82B are shown as measurement trace 204. As shown, during the first portion of trace 204 (i.e., from zero to approximately 40 mm), as the load on tube 74 was increased to approximately 15 Newtons the tube 74 stretched. After the tube had stretch approximately 40 mm, it began to slip out of device 82BA. Thus, device 82B could retain tube 74 until a pulling load of approximately 15 Newtons was applied, which is far better performance than the SecurAcath® device.

As should be understood from the foregoing, in addition to enhanced tube retention capacity, which is due in part to gripping features 118, 154, device 82 provides an ergonomic, easy to operate "snap-fit" design. Device 82 also is also easy to clean and inexpensive to manufacture using standard injection molding techniques. Finally, the design of device 82 permits efficient operation even after many uses (i.e., repeated assembly and disassembly).

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A tube securing device comprising:
  a base including a lower plate and a pair of inner walls, each of the inner walls including a ledge extending therefrom which forms a notch between the ledge and the lower plate, the base further including a groove between the inner walls sized to receive a tube in communication with a cavity of a patient; and
  a retainer including an upper plate having a planar top surface and the retainer also including a pair of retention beams, each of the retention beams including a ridge extending therefrom, the retainer further including a groove between the retention beams sized to receive the tube;
  wherein the tube is retained in the groove of the base and the groove of the retainer when the retainer is attached to the base by forcing the ridges over the ledges until the ridges snap into the notches; and wherein the lower plate of the base and the upper plate of the retainer form a pair of gaps between the base and the retainer when the retainer is attached to the base, the pair of gaps being configured to permit application of force to separate the retainer from the base.

2. The device of claim 1, further comprising an adhesive layer attached to the lower plate of the base, the adhesive layer including an adhesive configured to adhere the adhesive layer to the patient.

3. The device of claim 1, further comprising a tube receptacle having a first portion disposed within a recess formed in the base and a second portion disposed in a recess formed in the retainer, the groove of the base being formed in the first portion and the groove of the retainer being formed in the second portion.

4. The device of claim 3, wherein the first portion of the tube receptacle extends between a first end of the base and a second end of the base and the second portion of the tube receptacle extends between a first end of the retainer and a second end of the retainer.

5. The device of claim 3, wherein the tube receptacle is formed from a first material and the base and the retainer are formed from a second material.

6. The device of claim 5, wherein the first material is a rubber-like thermoplastic and the second material is a hard photopolymer.

7. The device of claim 1, wherein at least one of the groove of the base or the groove of the retainer includes at least one gripping feature.

8. A method of securing a tube to a patient, comprising:
placing the tube into a groove formed in a first component of a tube securing device;
placing a second component of the tube securing device onto the tube such that the tube is received by a groove in the second component;
applying a force to at least one of the first component and the second component to move the first component and the second component toward one another, thereby causing a pair of ridges of one of the first component or the second component to snap into a corresponding pair of notches of the other of the first component or the second component to connect the first component and the second component, the first component and the second component thereby forming a pair of gaps therebetween, the pair of gaps being configured to permit application of force to separate the first component from the second component; and
adhering one of the first component or the second component to the patient, the other of the first component or the second component having a planar top surface.

9. The method of claim 8, further comprising:
inserting a first portion of a tube receptacle into a recess in the first component, the first portion including the groove of the first component; and
inserting a second portion of a tube receptacle into a recess in the second component, the second portion including the groove of the second component.

10. The method of claim 9, wherein the first portion of the tube receptacle extends between a first end of the first component and a second end of the first component and the second portion of the tube receptacle extends between a first end of the second component and a second end of the second component.

11. The method of claim 9, wherein the tube receptacle is formed from a first material and the first and second components are formed from a second material.

12. The method of claim 11, wherein the first material is a rubber-like thermoplastic and the second material is a hard photopolymer.

13. The method of claim 8, wherein the first component includes a lower plate and a pair of inner walls, each of the inner walls including a ledge extending therefrom which forms one of the notches between the ledge and the lower plate, and the second component includes an upper plate and a pair of retention beams, each retention beam including one of the ridges.

14. The method of claim 13, wherein the groove of the first component is formed between the inner walls and the groove of the second component is formed between the retention beams.

15. The method of claim 8, wherein at least one of the groove of the first component or the groove of the second component includes at least one gripping feature.

16. A chest tube securing device comprising:
a base having a lower plate and a pair of inner walls extending form the lower plate and between a pair of end walls of the base, the base including a groove disposed between the inner walls and extending between the pair of end walls;
a retainer having an upper plate having a planar top surface and the retainer also including a pair of retention beams extending from the upper plate, the retainer including a groove disposed between the retention beams and extending between a pair of end surface of the retainer; and
an adhesive layer attached to a lower surface of the lower plate and having a lower surface with an adhesive layer;
wherein the tube is received within an opening formed by a groove in the base extending between the end walls and the groove in the retainer and secured in the chest tube securing device by mating engagement between a pair of notches formed by ledges extending from the inner walls of the base and a pair of ridges extending from the retention beams of the retainer;
wherein the lower plate of the base and the upper plate of the retainer form a pair of gaps between the base and the retainer when the retainer is attached to the base, the pair of gaps being configured to permit application of force to separate the retainer from the base.

17. The device of claim 16, further comprising a tube receptacle having a first portion disposed within a recess formed in the base and a second portion disposed in a recess formed in the retainer, the groove of the base being formed in the first portion and the groove of the retainer being formed in the second portion.

18. The device of claim 17, wherein the tube receptacle is formed from a first material and the base and the retainer are formed from a second material.

* * * * *